United States Patent [19]

Kleiner et al.

[11] Patent Number: 4,493,803
[45] Date of Patent: Jan. 15, 1985

[54] PROCESS FOR THE PREPARATION OF VINYLPHOSPHONIC ACID DIESTERS AND VINYLPHOSPHONIC ACID

[75] Inventors: Hans-Jerg Kleiner, Kronberg; Walter Dürsch, Königstein, both of Fed. Rep. of Germany

[73] Assignee: Hoechst Aktiengesellschaft, Frankfurt am Main, Fed. Rep. of Germany

[21] Appl. No.: 507,510

[22] Filed: Jun. 24, 1983

Related U.S. Application Data

[63] Continuation-in-part of Ser. No. 380,351, May 20, 1983, abandoned, and a continuation-in-part of Ser. No. 380,352, May 20, 1983, abandoned.

[30] Foreign Application Priority Data

May 22, 1981 [DE] Fed. Rep. of Germany ....... 3120438
May 22, 1981 [DE] Fed. Rep. of Germany ....... 3120437

[51] Int. Cl.³ .......................... C07F 9/38; C07F 9/40
[52] U.S. Cl. ............................. 260/968; 260/502.4 R
[58] Field of Search ............... 260/968, 983, 502.4 R

[56] References Cited

PUBLICATIONS

Yamagami et al., "Nippon Kagaka Kaisha," 10, (1972), p. 1991.
Canavan et al., "Jou. Chem. Soc. (London)," (1962), pp. 331–334.
Kosolapoff et al., "Organic Phosphorus Compounds," vol. 7, (1977), pp. 10, 11 & 22.

*Primary Examiner*—Anton H. Sutto
*Attorney, Agent, or Firm*—Curtis, Morris & Safford

[57] ABSTRACT

A method for making a vinylphosphonic acid diester of the formula $$CH_2=CH-P(O)(OR)_2$$

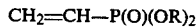

by heating a dialkyl 2-acetoxyethane phosphonate of the formula $$CH_3COOCH_2CH_2P(O)(OR)_2$$

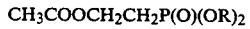

in the presence of an acidic or basic catalyst and reacting the resulting product with an orthoester of the formula $$R^1C(OR)_3.$$

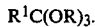

4 Claims, No Drawings

PROCESS FOR THE PREPARATION OF VINYLPHOSPHONIC ACID DIESTERS AND VINYLPHOSPHONIC ACID

This is a continuation-in-part application of U.S. patent application Ser. No. 380,351 and Ser. No. 380,352 filed May 20, 1983, now both abandoned.

It is known that vinylphosphonic acid derivatives can be prepared from 2-chlorethanephosphonic acid derivatives. However, the synthesis of these 2-chloroethanephosphonic acid derivatives is technically involved. A technically simpler route is via 2-acetoxyethanephosphonic acid diesters, which can be prepared from vinyl acetate and dialkyl phosphites (German Offenlegungsschrift No. 2,127,821). Dimethyl vinylphosphonate can then be obtained in a yield of only 50% from dimethyl 2-acetoxyethanephosphonate by elimination of acetic acid at 550° C. [M. Yamagami et al., Nippon Kagaku Kaisha 10, 1991 (1972)]. A new process is therefore sought which would make it possible to prepare vinylphosphonic acid diesters from 2-acetoxyethanephosphonic acid diesters in a higher yield.

It is also known that pure vinylphosphonic acid can be obtained from vinylphosphonic acid dichloride. However, the synthesis of pure vinylphosphonic acid dichloride is technically elaborate. A simpler process to prepare vinylphosphonic acid is therefore desirable, too.

It has now been found, surprisingly, that vinylphosphonic acid diesters of the general formula $$CH_2=CH-\overset{O}{\underset{\|}{P}}(OR)_2$$

in which R denotes alkyl groups having 1 to 4, preferably 1 to 2, carbon atoms, can be prepared in a simple and economical way by heating dialkyl 2-acetoxyethanephosphonates of the general formula $$CH_3COOCH_2CH_2\overset{O}{\underset{\|}{P}}(OR)_2$$

in which R has the abovementioned meaning, at 150° to 270° C., preferably 170° to 230° C., in the presence of acid or basic catalysts and reacting the resulting reaction product with orthoesters of the general formula $$R'C(OR)_3$$

in which R' denotes hydrogen or $C_1$-$C_4$-alkyl or $C_1$-$C_4$-alkoxy and R denotes alkyl groups having 1 to 4, preferably 1 to 2, carbon atoms, at 30° to 200° C.

In a further step, these vinylphosphonic acid diesters may be hydrolyzed with water at temperatures between 130° and 230° C., preferably between 140° and 175° C., while simultaneously distilling off the alcohols formed to get the free vinylphosphonic acid.

It is surprising that in this process the orthoesters are not added onto the vinylphosphonic acid group, since it is known that orthoesters can be added onto unsaturated compounds such as vinyl ethers or vinyl esters in the presence of acid catalysts (Houben-Weyl, Methoden der Organischen Chemie [Methods of Organic Chemistry], Volume VI/3, page 247-248, Georg Thieme Verlag Stuttgart, 1965).

Examples of possible starting materials are the dimethyl, diethyl, diisopropyl and di-n-butyl ester of 2-acetoxyethanephosphonic acid. Dimethyl 2-acetoxyethanephosphonate is particularly preferable. Examples of orthoesters which are particularly suitable are trimethyl orthoformate, triethyl orthoformate, trimethyl orthoacetate, triethyl orthoacetate, triethyl orthopropionate and tetramethyl orthocarbonate.

Numerous compounds are possible as acid or basic catalysts. Acid catalysts used can be:

(A) sulfuric acid or phosphoric acid (B) halogen-containing carboxylic acids having a $P_{Ka}$ value <2.5, such as dichloroacetic acid, trichloroacetic acid or trifluoroacetic acid (C) aromatic sulfonic acid having a $P_{Ka}$ value <2.5, such as benzenesulfonic acid or p-toluenesulfonic acid (D) preferably phosphonic acids having 2 to 18 carbon atoms, such as dimethylphosphonic acid, methylethylphosphinic acid, dioctylphosphinic acid, methylphenylphosphinic acid or diphenylphosphinic acid (E) particularly preferably phosphonic acids having 1 to 18 carbon atoms and their half-esters having 1 to 4 carbon atoms in the alcohol radical, such as methanephosphonic acid, propanephosphonic acid, propanephosphonic acid monomethyl ester, octadecanephosphonic acid, 2-acetoxyethanephosphonic acid, 2-acetoxyethanephosphonic acid monomethyl ester, vinylphosphonic acid, vinylphosphonic acid monomethyl ester, vinylphosphonic acid monoethyl ester or benzenephosphonic acid (F) likewise particularly preferably pyrophosphonic acids or their half-esters, such as methanepyrophosphonic acid, benzenepyrophosphonic acid, vinylpyrophosphonic acid or vinylpyrophosphonic acid monomethyl ester (G) acid reaction mixtures which are produced in the process according to the invention are also highly suitable.

Basic catalysts used can be:

(A) Tertiary aliphatic and aromatic amines and phosphines having 3 to 18 carbon atoms, such as trimethylamine, tripropylamine, tributylamine, triphenylamine, trimethylphosphine, triethylphosphine, tripropylphosphine, tributylphosphine, triphenylphosphine and tris-(p-diethylaminophenyl)-phosphine and the corresponding mixed amines, phosphines, phospholanes and phospholenes, such as dimethylethylamine, diethylbutylamine, N-dimethylaniline, 4-methyl-N-dimethylaniline, N-diethylaniline, N,N-tetramethylphenyldiamine or N-methylpyrrolidine, methyldiethylphosphine, dimethylpropylphosphine, diethylbenzylphosphine, 1-methylphosphol-3-ene and 1-ethyl-3-methylphosphol-3-ene.

(B) Quarternary ammonium salts and phosphonium salts having 3 to 18 carbon atoms, such as tetramethylammonium chloride, tetramethylammonium bromide or tetraethylphosphonium chloride, trimethylbenzylammonium chloride, triethylbenzylammoniumchloride, triethylbenzylammonium bromide, trimethylbenzylphosphonium chloride or triphenylethylphosphonium 2,4-diaminobenzenesulfonate.

(C) Heterocyclic compounds having aromatic character, such as pyridine, quinoline, their various alkyl and dialkyl, preferably methyl or dimethyl derivatives, imidazole, N-vinylimidazole, benzothiazole, 2-amino-6-ethoxybenzothiazole, and also phosphabenzenes.

(D) Acid amides, such as dimethylformamide, N-dimethylacetamide, N-diethylpropionamide, N-dimethylbenzamide, N-methylpyrrolidone or N,N'-tetramethylterephthalic acid diamide or ureas, such as tetramethylurea or trimethylphenylurea.

(E) Other nitrogen compounds or phosphorus compounds having a higher valency of one N atom or P atom than 3, such as pyridine-N-oxide, trimethylphosphine oxide, tributylphosphine oxide, trihexylphosphine oxide, triphenylphosphine oxide, dimethylphenylphosphine oxide, dimethylphenylphosphine sulfide, dimethylchloromethylphosphine oxide, dimethyleicosylphosphine oxide, dimethyldodecylphosphine oxide, dimethylphosphine oxide, dimethylpyrrolidinyl-1-methylphosphine oxide, triphenylphosphine dichloride, dimethyldodecylphosphine sulfide, triphenylphosphineimine, dimethylchlormethylphosphine dichloride, N-2-dimethylphosphinylethylmethylacetamide or N-2-dimethylphosphinylethylmethylamine, or phospholene oxide, such as 1-methylphosphol-1-ene oxide or 1-ethyl-3-methylphosphol-1-ene oxide.

(F) Amides of phosphinous and phosphonous acid and of phosphinic and phosphonic acids and also their thioanalogs, such as ethanephosphonic acid bis-diethylamide, methanebutanephosphinous acid dimethylamide or diethylphosphinous acid isobutylamide. Also triamides of phosphoric and of thiophosphoric acid, such as hexamethylphosphoric acid triamide.

The catalysts are used in amounts of 0.01 to 10, preferably 0.1 to 5, % by weight. When vinylphosphonic acid, monoalkyl esters thereof or acid reaction mixtures already obtained are used, even larger amounts of 10 to 50% by weight can be used.

The process is in general carried out by mixing the starting material with the catalyst and raising the mixture to the required reaction temperature of 150° to 270° C., preferably 170° to 230° C.

Higher temperatures are possible, but they do not yield any benefit. The danger of an increased formation of by-products, and also of polymerization, then arises.

This reaction eliminates an alkyl acetate and essentially produces a vinylphosphonic acid half-ester. The alkyl acetate is distilled off together with small amounts of an alkanol and of a dialkyl ether. The distillation is carried out under atmospheric pressure, if appropriate with the aid of an inert gas, such as, for example, nitrogen. However, in particular cases it may be advantageous to distil off in vacuo. The elimination of the alkyl acetate is complete after 2 to about 20 hours. It can be advantageous to continue stirring thereafter for another 1 to 4 hours at the reaction temperature. The process can also be carried out in a continuous manner. To prevent polymerization, it is advantageous to add corresponding inhibitors, such as, for example, hydroquinone, hydroquinone monomethyl ether or phenothiazine.

If 2-acetoxyethanephosphonic acid diesters which are contaminated from their preparation with small amounts of the corresponding monoester are used as a starting material, a further addition of a catalyst is not necessarily required. It is here advantageous to start the reaction at about 250° C. When the acid reaction product which actually also acts as a catalyst for the elimination has been formed to a sufficient extent, the process can be continued at lower temperatures, for example at 180° to 220° C.

The crude vinylphosphonic acid half-ester produced in the first stage is reacted with the orthoesters at 30° to 200° C., and carboxylates or carbon dioxide and the corresponding alcohols are formed at the same time. In the reaction to give the carboxylates and alcohols, it is advantageous to operate within a temperature range which is such that the carboxylates and alcohols distil off after they have been formed. As a rule at least one mole, preferably 1.5 to 2 moles, of orthoester are used per mole of vinylphosphonic acid half-ester. Excesses which are greater yield no essential benefit. A particularly advantageous method of carrying out the reaction is to mix the half-ester with approximately the same amount of fully formed vinylphosphonic acid diester, in the state in which it is obtained as reaction product, and to leave the mixture for about 1 hour at an elevated temperature, for example at 160° C., and thereafter to react this reaction mixture eith the orthoester. In this procedure, the amount of dialkyl ether which is otherwise necessarily obtained is small, and the exploitation of the alkylating potential of the orthoester is very high. It is also possible to mix the crude vinylphosphonic acid half-ester with the orthoester, that is initially to introduce the orthoester and to meter in the vinylphosphonic acid half-ester, or vice versa, and to allow the resulting mixture to react to completion at the particular reaction temperature required. When using orthocarbonates, this reaction temperature is at about 30° to 90° C., while in the case of orthoformate and the higher orthocarboxylates a temperature of about 30° to 160° C. is required. The process can also be carried out in a continuous manner.

The vinylphosphonic acid diesters obtained in the present process are purified by distillation. As a rule, they contain relatively small amounts of trialkyl phosphates which, if it is desired, can be separated off by suitable methods, for example by distillation methods.

The dialkyl vinylphosphonates prepared in this process step and any trialkyl phosphates present then may be reacted in a further step with water at the reaction temperature required and the resulting alcohol is advantageously distilled off via a column. Small amounts of a dialkyl ether and olefins can be formed in this reaction. The reaction with water is complete when no more alcohol is split off. Here it can be advantageous to add relatively large amounts of water toward the end of the reaction and to distill off some of the unreacted water together with the alcohol. The pressure to be used in this process is not critical but the process is preferably carried out under approximately atmospheric pressure. In this process stage also it is advantageous to admix an amount of final product, namely vinylphosphonic acid, to the dimethyl vinylphosphonate before the hydrolysis.

The reaction temperatures in this process step are between 130° and 230° C. The reaction is preferably carried out within a temperature range of 140° to 175° C. The reaction with water can also be carried out in a continuous manner. The resulting vinylphosphonic acid can be freed from relatively small amounts of dissolved water in vacuo at an elevated temperature. The acid contains phosphoric acid as a secondary constituent if the trialkyl phosphate was not separated from the vinylphosphonic acid diester before the hydrolysis. It is possible to separate the phosphoric acid from the vinylphosphonic acid via the salts.

Dialkyl vinylphosphonates have long been well known intermediates in the preparation of, for example, flame-retardants, flotation auxiliaries and dyestuffs. They are also known as comonomers in the preparation of numerous synthetic polymers.

Vinylphosphonic acid is suitable for use as a corrosion inhibitor in aqueous systems and, in particular, also as an intermediate in the preparation of flame-retardants. Vinylphosphonic acids can also be converted into polyvinylphosphonic acid for which there are many industrial uses.

EXAMPLE 1

100 g of dimethyl-2-acetoxyethanephosphonate were heated with stirring at 220°–230° C. A mixture of 200 g of dimethyl 2-acetoxyethanephosphonate and 3 g of 4-(dimethylamino)-pyridine were added dropwise in the course of 6 hours and 112 g of methyl acetate distilled off over the same time period. 6 g of dimethyl ether were collected in a cold trap downstream from the apparatus. 171 g of crude monomethyl vinylphosphonate remained. 80 g of this reaction product and 93 g of trimethyl orthoacetate were mixed and the mixture was heated gradually, in the course of 4.5 hour and with stirring, to an internal temperature of 150° C. while methyl acetate and methanol distilled off. Another 35 g of trimethyl orthoacetate were then added at room temperature (molar ratio of monomethyl vinylphosphonate to orthoester was about 1:1.6) and the mixture was again gradually heated to 150° C. while methyl acetate distilled off. A total of 90 g of a mixture of methyl acetate and methanol were obtained. The residue was distilled under 0.5 mm Hg. 86 g of dimethyl vinylphosphonate were obtained which, according to the $^{31}$P-NMR spectrum, contained 7% of trimethyl phosphate. The distillation residue was 7 g. The yield of pure dimethyl vinylphosphonate was 83.5% of theory, relative to the amount of dimethyl 2-acetoxyethanephosphonate started with.

EXAMPLE 2

276 g of crude monomethyl vinylphosphonate, which had been prepared as in Example 1, were mixed with 376 g of trimethyl orthoformate, and the mixture was gradually heated in the course of 8 hours with stirring to 150° C. while methyl formate and methanol distilled off. Another 100 g of trimethyl orthoformate (molar ratio of monomethyl vinylphosphonate to orthoester was about 1:2) were then added at room temperature, and the temperature was gradually increased in the course of 13 hours to 150° C. while methyl formate and methanol distilled off. The residue was distilled under 0.5 mm Hg. 273 g of dimethyl vinylphosphonate were obtained which, according to the $^{31}$P-NMR spectrum, contained 6% of trimethyl phosphate. The distillation residue was 47 g. The yield of pure dimethyl vinylphosphonate was 76% of theory, relative to the amount of crude monomethyl vinylphosphonate started with.

EXAMPLE 3

150 g of tetramethyl orthocarbonate were added dropwise with stirring at room temperature to 80 g of crude monomethyl vinylphosphonate, which had been prepared as in Example 1. The temperature increased slightly to 35° C. and carbon dioxide was eliminated at the same time. The temperature was then gradually increased in the course of about 2.5 hours to 87° C. while carbon dioxide continued to be eliminated. The mixture was then distilled under 0.5 mm Hg. This produced 74 g of dimethyl vinylphosphonate and, in a cold trap downstream of the apparatus, a mixture of about 30 g of methanol and 77 g of unconverted tetramethyl orthocarbonate. The reaction of the 80 g of crude monomethyl vinylphosphonate used as starting material thus consumed 73 g of tetramethyl orthocarbonate (molar ratio of monomethyl vinylphosphonate to orthoester was 1:0.8).

EXAMPLE 4

25 g of vinylphosphonic acid and 70 g of diethyl 2-acetoxyethanephosphonate were heated with stirring to 180° C. 252 g of diethyl 2-acetoxyethanephosphonate were then slowly added dropwise over 14 hours while the temperature gradually increased to 200° C. and ethyl acetate distilled off. The mixture was then stirred for 9 hours at 190° C. 190 g of crude monoethyl vinylphosphonate were obtained. Distillation produced 128 g of ethyl acetate and additionally 8 g of light ends which were trapped in a cold trap downstream from the apparatus. 95 g of the crude monoethyl vinylphosphonate and 124 g of triethyl orthoformate were refluxed for 8 hours at about 75° C. The temperature was then gradually increased in the course of 5.5 hours to 150° C. while ethyl acetate and ethanol distilled off. A further 100 g of triethyl orthoformate were then added at room temperature and the mixture was gradually heated again to 150° C. while light ends distilled off. A cold trap downstream from the apparatus collected less that 1 g. The mixture was then distilled and 96.5 g of diethyl vinylphosphonate were obtained. This corresponded to a yield of about 70%, relative to the amount of vinylphosphonic acid and diethyl 2-acetoxyethanephosphonate started with. During the reaction with the orthoester, about 160 g distilled off which contained 28 percent of ethanol and about 10 percent of diethyl ether in addition to about 60 percent of ethyl formate.

EXAMPLE 5

80 g of crude monomethyl vinylphosphonate as obtained in Example 1 were mixed with 80 g of the dimethyl vinylphosphonate obtained according to Example 1, and the mixture was kept at 160° C. for 2 hours. The resulting mixture was added dropwise with stirring in the course of 6 hours to 148 g of trimethyl orthoformate at 100° C. During this period 93 g of a mixture of methyl acetate and methanol distilled off. No light ends were observed in a cold trap downstream from the apparatus. The mixture was then heated to 145° C. and finally distilled. 153 g of dimethyl vinylphosphonate and 22 g of distillation residue were obtained. The cold trap of the distillation apparatus contained 22 g of essentially trimethyl orthoacetate. 73 g of dimethyl vinylphosphonate were obtained.

EXAMPLE 6

30 g of vinylphosphonic acid and 80 g of diethyl 2-acetoxyethanephosphonate were mixed, and the mixture was heated with stirring to 175°–180° C. 500 g of diethyl 2-acetoxyethanephosphonate were then added dropwise in the course of 4 hours at this temperature, 13 hours at 185° C. and 6 hours at 190° C., while 187 g of ethyl acetate distilled off. 2 g of light ends were collected in a cold trap downstream from the apparatus. The resulting reaction mixture (305 g) was maintained for a further 1 hour at 200° C. 295 g of crude monoethyl vinylphosphonate were then obtained. 81 g of this product were mixed with 106 g of triethyl orthoformate, and the mixture was heated with stirring for 7 hours up to 150° C. while ethyl formate and ethanol distilled off. A further 60 g of trimethyl orthoformate were then added at room temperature, and the resulting mixture was again heated for 2 hours up to 150° C. A total of 109 g of ethyl formate together with ethanol and diethyl ether were distilled off. Distillation of the reaction mixture produced 81 g of diethyl vinylphosphonate which contained relatively small amounts of triethyl phosphate.

EXAMPLE 7

100 g of dimethyl 2-acetoxyethanephosphonate were heated with stirring at 220° to 230° C. A mixture of 200 g of dimethyl 2-acetoxyethanephosphonate and 3 g of 4-(dimethylamino)-pyridine were added dropwise in the course of 6 hours and 112 g of methyl acetate distilled off over the same time period. 6 g of dimethyl ether were collected in a cold trap downstream from the apparatus, 171 g of crude monomethyl vinylphosphonate remained. This quantity was mixed with 200 g of methyl orthoacetate, and the resulting mixture was gradually heated in the course of 4.5 hours with stirring to an internal temperature of 150° C. while a mixture of methanol and methyl acetate distilled off. A further 70 g of trimethyl orthoacetate were then added at room temperature (molar ratio of monomethyl vinylphosphonate to orthoester was about 1:1.6) and the mixture was again gradually heated to 150° C. while methyl acetate and methanol distilled off. A total of 192 g of a mixture of methanol and methyl acetate were obtained. The residue was distilled off under 0.5 mm Hg. 172 g of dimethyl vinylphosphonate were obtained which, according to a $^{31}$P-NMR spectrum, contained 7% of trimethyl phosphate. These 172 g of dimethyl vinylphosphonate were mixed with 17 g of vinylphosphonic acid, and the mixture was heated with stirring at 160° to 175° C. Water was metered in at the same time, while methanol distilled off via a column with a silver-coated jacket. 12 g of dimethyl ether were collected in cold trap downstream from the apparatus. After about 7 hours, the water contained in the reaction mixture was distilled off at 90° C. and under 0.5 mm Hg. 153 g of vinylphosphonic acid remained which had a content of 7% of phosphoric acid and 2% of the compound

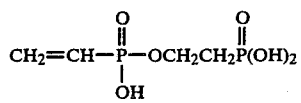

as measured from the $^{31}$P-NMR spectrum.

EXAMPLE 8

350 g of dimethyl vinylphosphonate, as prepared in Example 7, and 35 g of vinylphosphonic acid were mixed, and the mixture was heated with stirring to 145° C. Water was then metered in for 14 hours while methanol distilled off via a column with a silver-coated jacket. 3 g of dimethyl ether were collected in a cold trap downstream from the apparatus. The water containing the reaction mixture was then distilled off at 90° C. and under 0.5 mm Hg. 310 g of vinylphosphonic acid remained.

We claim:

1. A method for making a vinylphosphonic acid diester of the formula $$CH_2=CH-P(O)(OR)_2$$

wherein R is $C_1$–$C_4$-alkyl, which method comprises heating a dialkyl-2-acetoxyethane-phosphonate of the formula $$CH_3COOCH_2CH_2P(O)(OR)_2$$

at a temperature from 150° C. to 270° C. in the presence of an acidic or basic catalyst to form a vinylphosphonic acid monoester, and then reacting this monoester with an orthoester of the formula $$R^1C(OR)_3,$$

wherein $R^1$ is hydrogen, $C_1$–$C_4$-alkyl, or $C_1$–$C_4$-alkoxy, at a temperature from 30° to 200° C.

2. A method as in claim 1 wherein said phosphonate is heated to a temperature from 170° to 230° C.

3. A method as in claim 1 wherein said diester is subsequently hydrolyzed by reacting with water at a temperature from 130° to 230° C. while distilling off the alcohol formed thereby.

4. A method as in claim 3 wherein said diester is hydrolyzed at a temperature between 140° and 175° C.

* * * * *